(12) United States Patent
Hsu et al.

(10) Patent No.: US 9,642,972 B2
(45) Date of Patent: May 9, 2017

(54) NEEDLE PROTECTING MODULE OF AN INJECTING DEVICE AND AN INJECTION DEVICE WITH A NEEDLE PROTECTING MODULE

(71) Applicants: Pei-Yang Hsu, Taichung (TW); Pei-Hsin Hsu, Taichung (TW); Wei-Ni Hsu, Taichung (TW)

(72) Inventors: Pei-Yang Hsu, Taichung (TW); Pei-Hsin Hsu, Taichung (TW); Wei-Ni Hsu, Taichung (TW)

( * ) Notice: Subject to any disclaimer, the term of this patent is extended or adjusted under 35 U.S.C. 154(b) by 621 days.

(21) Appl. No.: 14/069,672

(22) Filed: Nov. 1, 2013

(65) Prior Publication Data

US 2014/0243752 A1   Aug. 28, 2014

(30) Foreign Application Priority Data

Feb. 23, 2013   (TW) .............................. 102106404 A

(51) Int. Cl.
*A61M 5/32* (2006.01)

(52) U.S. Cl.
CPC ..... *A61M 5/326* (2013.01); *A61M 2005/3267* (2013.01); *A61M 2207/00* (2013.01)

(58) Field of Classification Search
CPC .......... A61M 5/326; A61M 2005/3267; A61M 2207/00; A61M 2005/2073; A61M 5/3272
See application file for complete search history.

(56) References Cited

U.S. PATENT DOCUMENTS

| 9,155,838 B2 * | 10/2015 | Bilton .................. A61M 5/2448 |
| 9,186,459 B2 * | 11/2015 | Bechmann .......... A61M 5/2033 |
| 2013/0041321 A1 * | 2/2013 | Cross .................. A61M 5/2448 |
| | | 604/189 |

* cited by examiner

*Primary Examiner* — Emily Schmidt
*Assistant Examiner* — Lauren M Peng
(74) *Attorney, Agent, or Firm* — patenttm.us

(57) ABSTRACT

A needle protecting module of an injection device in connecting with a syringe has a needle base, a needle body a tube module, a mounting tube, an elastic unit, and a stopping unit. The syringe has a tube body and an axis. The needle body transfixes the needle base and communicates with the tube body for medication injection. The needle base is removably engaged with the tube body and bearing the needle protecting module is transfixed by the needle body. The tube module is mounted around the needle base and has an annular space. The mounting tube is movably inserted into the annular space. The elastic unit is mounted in the annular space and abuts both the mounting tube and the needle base bilaterally. The stopping unit is moveably mounted in the annular space and is selectively engaged with the mounting tube.

18 Claims, 19 Drawing Sheets

NEEDLE PROTECTING MODULE OF AN INJECTING DEVICE AND AN INJECTION DEVICE WITH A NEEDLE PROTECTING MODULE

BACKGROUND OF THE INVENTION

1. Field of the Invention

The present invention relates to an injection device, and more particularly for a needle protecting module of an injection device and an injection device with a needle protecting module for facilitating a safe injection practice.

2. Description of Related Art

With reference to FIGS. 18 and 19, a conventional syringe 1 has a tube body 10, a pushing stick module 11, a needle base 12, a needle body 13, an isolating tube 14, an inner tube 15, an outer tube 16, an elastic unit 17, a mounting tube 18, and a stopping unit 19. The pushing stick module 11 is slidably and airtightly mounted in the tube body 10. The needle base 12 is mounted around the front end of the tube body 10. The needle body 13 is connected with the needle base 12 parallel with the axis X of the tube body 10. The isolating tube 14 is connected with the needle base 12 and surrounds the needle body 13. The inner tube 15 is connected with the needle base 12 and surrounds the isolating tube 14. The outer tube 16 is connected with the needle base 12 and surrounds the isolating tube 14. The elastic unit 17 is inserted between the isolating tube 14 and the inner tube 15. The mounting tube 18 is inserted between the isolating tube 14 and the inner tube 15.

A first stopping surface 181 of the mounting tube 18 faces a tapered section 151 of the inner tube 15. A second stopping surface 182 of the mounting tube 18 faces a flange 161 of the outer tube 16. An abutting surface 191 of the stopping unit 19 selectively abuts the first stopping surface 181. A recessed portion 194 is formed between two inclined surfaces 192 and 193 and selectively abuts the tapered section 151.

Before injection, the elastic unit 17 abuts the mounting tube 18, such that the second stopping surface 182 abuts the flange 161, and the tapered section 151 abuts and is engaged with the recessed portion 194. Therefore, the stopping unit 19 is fixed in position. Also, the abutting surface 191 abuts the first stopping surface 181, such that the mounting tube 18 is also fixed in position.

During injection, the mounting tube 18 is pressed against the skin of the patient to push the stopping unit 19. The inclined surface 193 pushes the tapered section 151 to expand the inner diameter of the tapered section 151, such that the first stopping surface 181 can be inserted into the tapered section 151. Therefore, the mounting tube 18 can be inserted into the inner tube 15 during the injection process.

After injection, the elastic unit 17 pushes the mounting tube 18 to move away from the needle base 12. The first stopping surface 181 and the second stopping surface 182 are restricted by the tapered section 151 and the flange 161 respectively, such that the mounting tube 18 cannot move since the mounting tube 18 is left without the guiding of the stopping unit 19. Therefore, the mounting tube 18 can shelter the needle body 13 to isolate the needle body 13 away from the patient and the user.

However, the space between the isolating tube 14 and the inner tube 15 has to be large enough for accommodating the stopping unit 19 mounted between the isolating tube 14 and the inner tube 15, and the space also has to be reserved for elastic radial deformation of the inner tube 15 at the tapered section 151.

On the other hand, if the radial deformation is excessive, the mounting tube 18 cannot move smoothly. If the radial deformation is insufficient, the mounting tube 18 cannot be stopped effectively, such that the needle body 13 may be exposed outside. Therefore, the drawbacks of the conventional syringe 1 have to be resolved indeed.

SUMMARY OF THE INVENTION

The main objective of the present invention is to provide a needle protecting module of an injection device and an injection device with a needle protecting module to resolve the aforementioned problems and further facilitate a safe clinical injection practice.

The needle protecting module of an injection device has a needle base, a needle body, a tube module, a mounting tube, an elastic unit, and a stopping unit The needle body transfixes the needle base and is able to communicate with an injection device for medication injection.

The tube module is mounted around the needle base and has a first annular surface formed as a periphery, a second annular surface formed as a periphery and surrounding the first annular surface, an annular space formed between the first annular surface and the second annular surface, a first tube stepped surface formed radially on the first annular surface, and a second tube stepped surface formed radially on the second annular surface.

The mounting tube is hollow, is movably inserted into the annular space and has a first engagement surface formed on an interior of the mounting tube and a second engagement surface formed on an exterior of the mounting tube.

The elastic unit is mounted in the annular space and abuts both the mounting tube and the needle base bilaterally.

The stopping unit is moveably mounted in the annular space and selectively engaged with the mounting tube.

The injection device with a needle protecting module for a safe injection has a syringe, a needle body, a needle base, a tube module, a mounting tube, an elastic unit, and a stopping unit.

The syringe has a tube body and an axis.

The needle body communicates with the tube body for medication injection, and is parallel with the axis of the syringe.

The needle base is formed removably engaged with the tube body, is parallel with the axis, and is transfixed through by the needle body.

The tube module is mounted around the needle base and has a first annular surface formed as a periphery and being parallel with the axis, a second annular surface formed as a periphery, being parallel with the axis and surrounding the first annular surface, an annular space formed between the first annular surface and the second annular surface, a first tube stepped surface formed radially on the first annular surface, and a second tube stepped surface formed radially on the second annular surface.

The mounting tube is hollow, is movably inserted into the annular space and has a first engagement surface formed on an interior of the mounting tube, a second engagement surface formed on an exterior of the mounting tube.

The elastic unit is mounted in the annular space and abuts between the mounting tube and the needle base.

The stopping unit is moveably mounted in the annular space perpendicular to the axis and selectively engaged with the mounting tube.

The injection device with a needle protecting module for safe injection has a syringe, a needle body, a needle base, a tube module, a mounting tube, an elastic unit and a stopping unit.

The syringe has a tube body and an axis.

The needle body communicates with the tube body for medication injection, and is parallel with the axis of the syringe.

The needle base is removably engaged with the tube body, is parallel with the axis and transfixed by the needle body.

The tube module is mounted around the needle base and has a first annular surface, a second annular surface, an annular space, a first tube stepped surface, and a second tube stepped surface. The first annular surface is formed as a periphery and is parallel with the axis. The second annular surface is formed as a periphery, is parallel with the axis and surrounding the first annular surface. The annular space is formed between the first annular surface and the second annular surface. The first tube stepped surface is formed radially on the first annular surface. The second tube stepped surface is formed radially on the second annular surface. The mounting tube is hollow, is movably inserted into the annular space and having a first engagement surface formed on an interior of the mounting tube and a second engagement surface formed on an exterior of the mounting tube.

The elastic unit is mounted in the annular space and abuts both the mounting tube and the needle base bilaterally.

The stopping unit is moveably mounted in the annular space perpendicular to the axis and is selectively engaged with the mounting tube.

Other objectives, advantages and novel features of the present invention will become more apparent from the following detailed description when taken in conjunction with the accompanying drawings.

DETAILED DESCRIPTION OF PREFERRED EMBODIMENT

Figure 1:
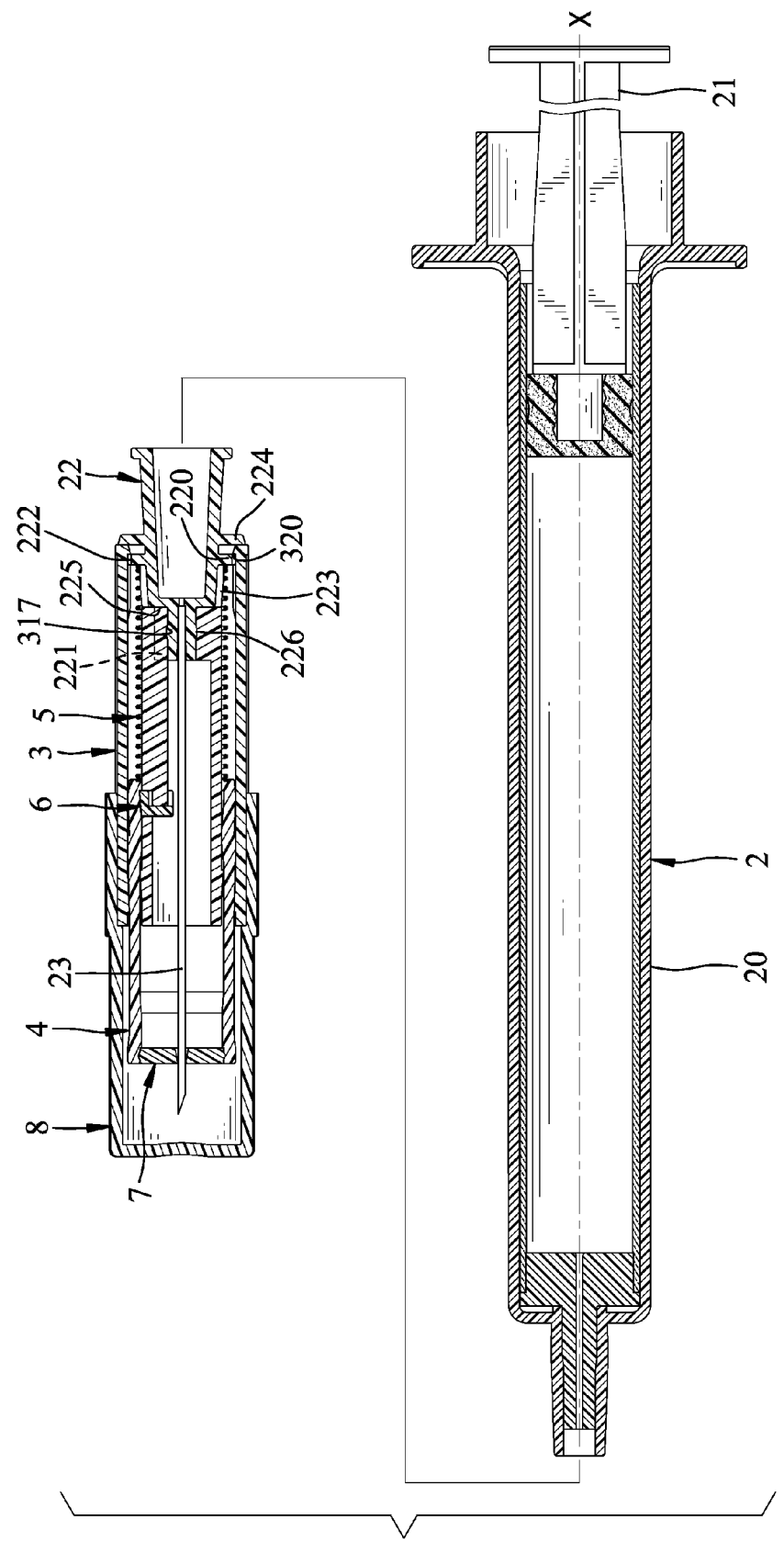
FIG. 1 is an exploded side view in partial section of a first preferred embodiment of a needle protecting module of an injection device in accordance with the present invention in connecting with a syringe.
Figure 2:
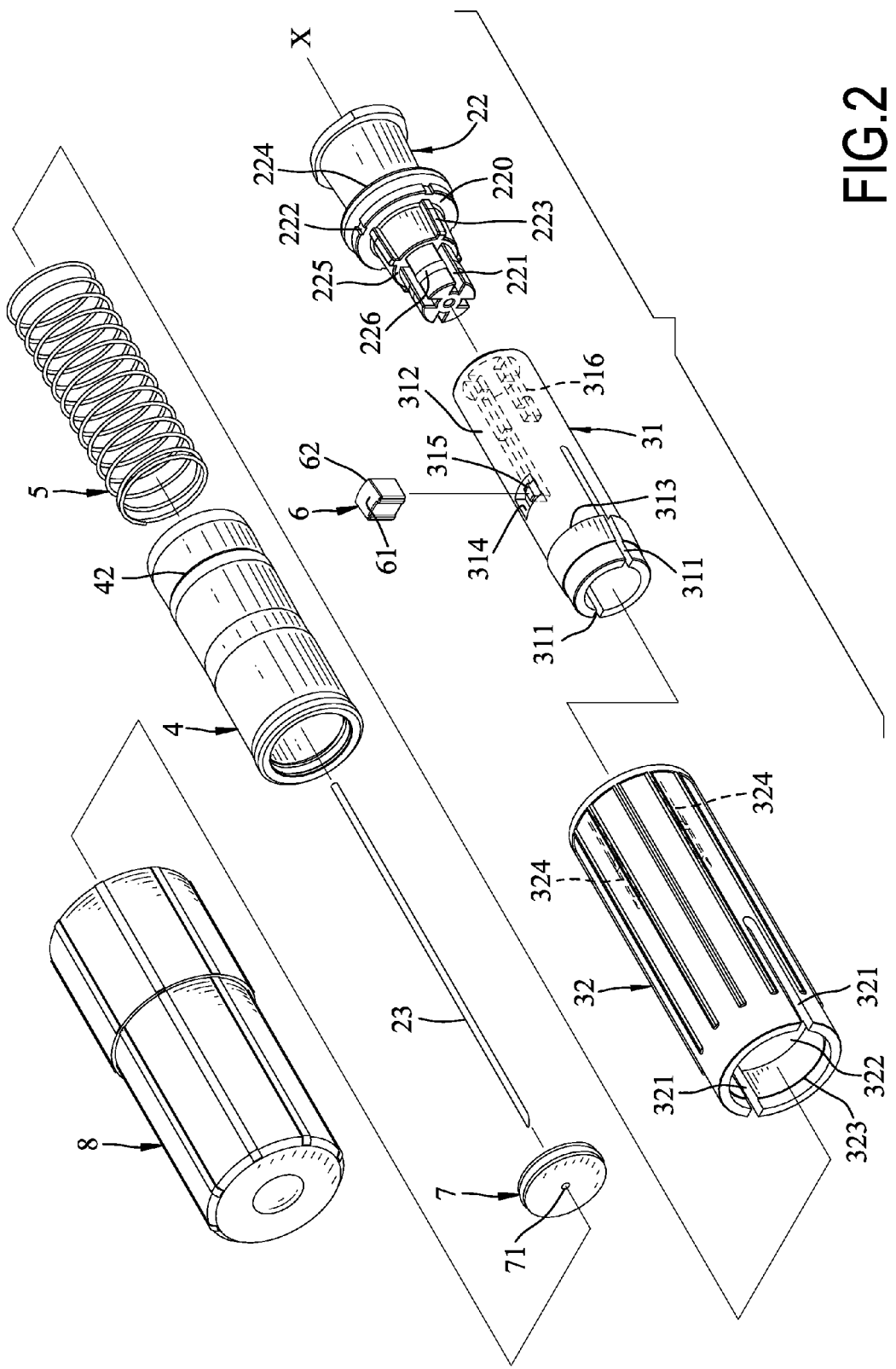
FIG. 2 is a partially exploded perspective view of the needle protecting module of an injection device in FIG. 1.
Figure 3:
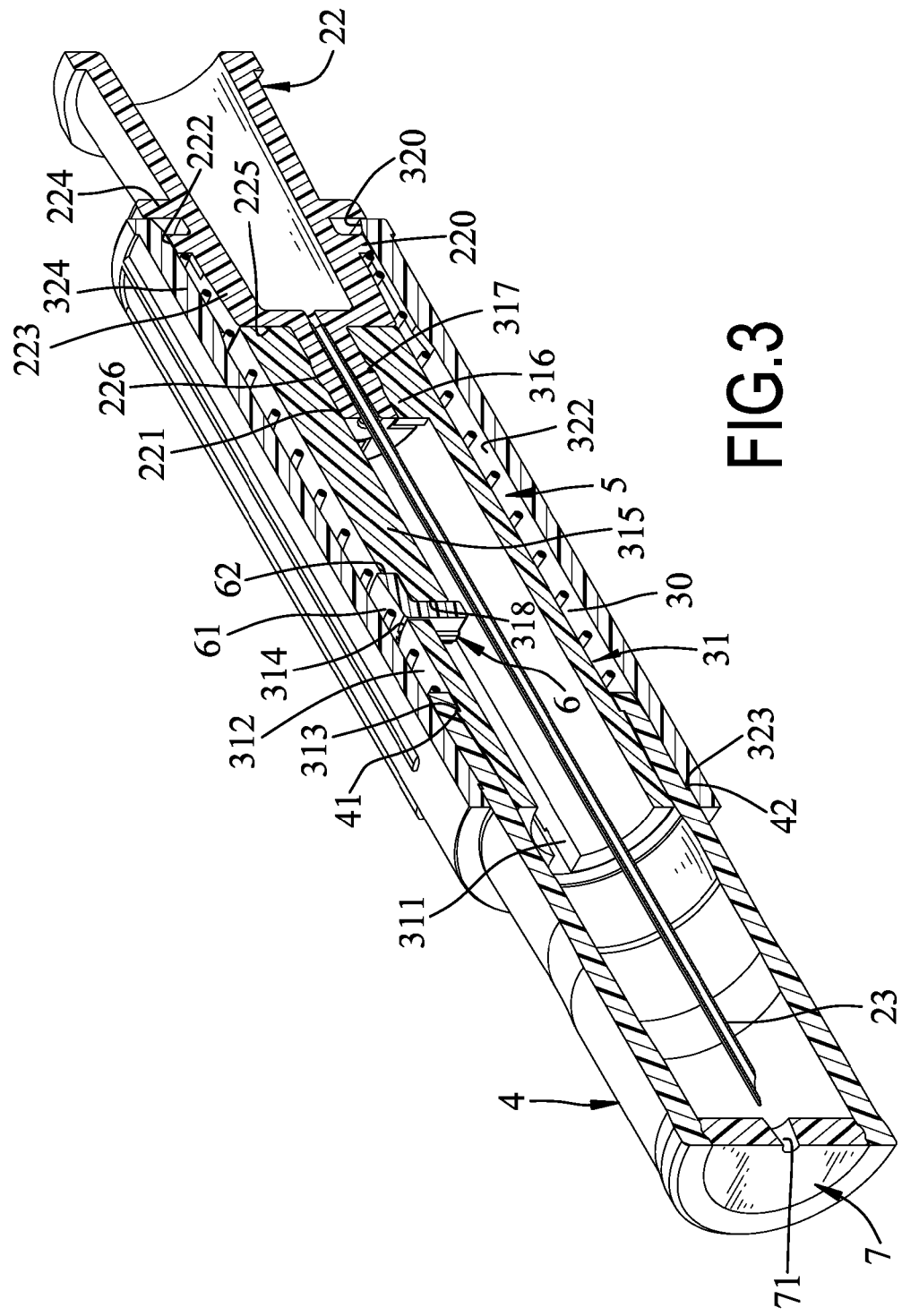
FIG. 3 is a cross sectional perspective view of the needle protecting module of an injection device in FIG. 1.

With reference to FIGS. 1 to 3, a first preferred embodiment of a needle protecting module of an injection device in accordance with the present invention comprises a needle base 22, a needle body 23, a tube module 3, a mounting tube 4, an elastic unit 5, a stopping unit 6, a cover 7, and a mounting cover 8.

Figure 4:
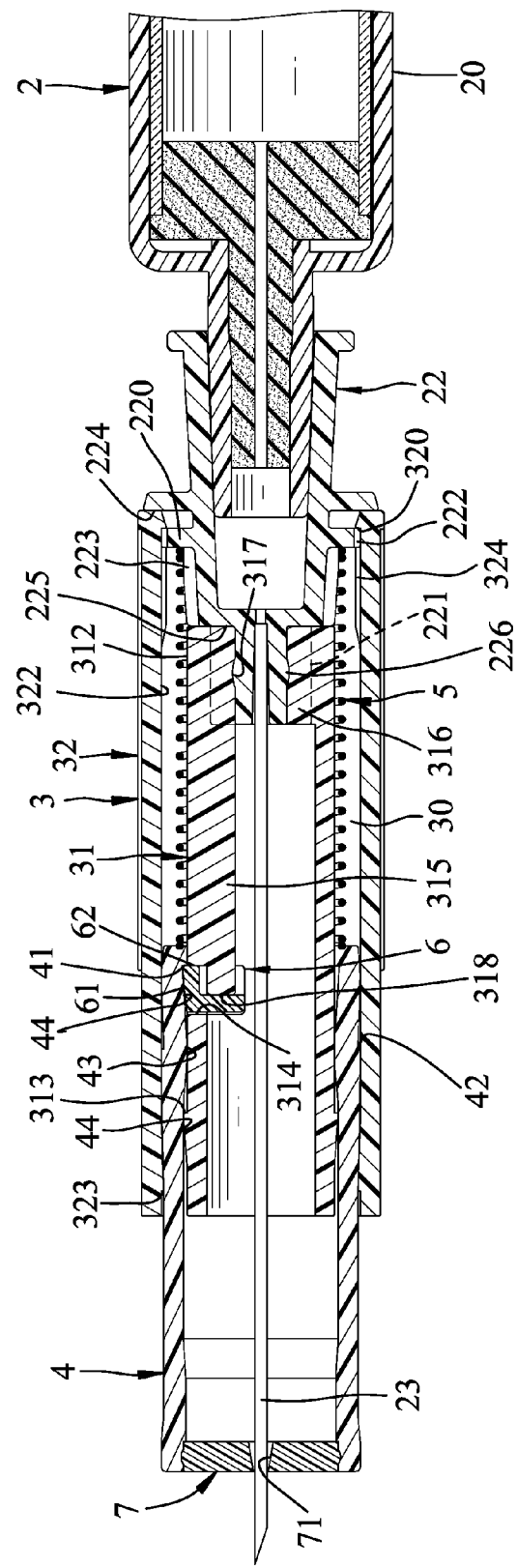
FIG. 4 is an enlarged side view in partial section of the needle protecting module of an injection device in FIG. 1 in an engagement with a syringe.

With reference to FIGS. 1 and 4, the needle protecting module can be removably connected with an injection device, a syringe 2 for this example for a safe injection practice. The syringe 2 has a tube body 20, an axis X, and a pushing stick module 21. The pushing stick module 21 is slidably and airtightly mounted in the tube body 20 parallel with the axis X.

The needle body 23 in communication with the tube body 20 is parallel with the axis X and can penetrate out of the needle protecting module for medication injection The needle base 22 is formed enabling to be removablely engaged with the tube body 20 and is transfixed by the needle body 23, and parallels with the axis X. The needle base 22 has a plate 220, a stopping surface 224, multiple first base engagement portions 222, multiple base ribs 223, a base stepped surface 225, multiple second base engagement portions 221, and an annular flange 226. The plate 220 is circular and is mounted in the middle of the needle base 22. The stopping surface 224 is formed on the rear side of the plate 220. The diameter of the stopping surface 224 is larger than the diameter of the plate 220. The first base engagement portions 222 are formed on the periphery of the plate 220 and may be blocks or recesses. The base ribs 223 longitudinally protrude from the needle base 22, parallel with the axis X and are located at the front side of the plate 220 opposite to the stopping surface 224. The base stepped surface 225 is formed on the needle base 22 and is connected with the front sides of the base ribs 223. The second base engagement portions 221 are longitudinally connected with the base stepped surface 225, parallel with the axis X and can be blocks or grooves. The annular flange 226 protrudes from the needle base 22 radially and is adjacent to the front end of the needle base 22.

The tube module 3 is mounted around the needle base 22 removably parallel the axis X and has an inner tube 31 and an outer tube 32. The inner tube 31 is hollow, is mounted around the needle base 22 and has a first annular surface 312, a first tube stepped surface 313, two first slits 311, a tube hole 314, a tube rib 315, an abutted surface 318, two first tube engagement portions 316, and an annular recess 317.

The first annular surface 312 is formed on the exterior of the inner tube 31 and parallels the axis X. The first tube stepped surface 313 is formed radially on the first annular surface 312 and is adjacent to the front end of the inner tube 31. The first slits 311 are longitudinally formed in the front end of the inner tube 31 and are parallel with the axis X. The tube hole 314 is formed through the first annular surface 312. The tube rib 315 is longitudinally formed on the interior of the inner tube 31 and extends to the tube hole 314. The abutted surface 318 is formed on the front end of the tube rib 315. The first tube engagement portions 316 are longitudinally formed on the interior of the inner tube 31 and are engaged with and match the second base engagement portions 221 to keep the inner tube 31 from rotating relative to the needle base 22. The tube rib 315 may extend from one of the first tube engagement portions 316. The annular recess 317 is formed on the interior of the inner tube 31 radially and is engaged with the annular flange 226.

The outer tube 32 is hollow, is mounted around the needle base 22, surrounds the inner tube 31 and has a second annular surface 322, a second tube stepped surface 323, a tube engagement rib 320, two second slits 321, and two second tube engagement portions 324. The second annular surface 322 is formed on the interior of the outer tube 32. The second tube stepped surface 323 is formed radially on the second annular surface 322, and is adjacent to the front end of the outer tube 32. The tube engagement rib 320 is formed on the second annular surface 322 and is engaged with the needle base 22. The second slits 321 are longitudinally formed in the front end of the outer tube 32 and are parallel with the axis X. The second tube engagement portions 324 are formed on the second annular surface 322, match and are engaged with the first base engagement portions 222 to keep the outer tube 32 from rotating relative to the needle base 22. The tube module 3 further has an annular space 30 formed between the second annular surface 322 and the first annular surface 312.

Figure 5:
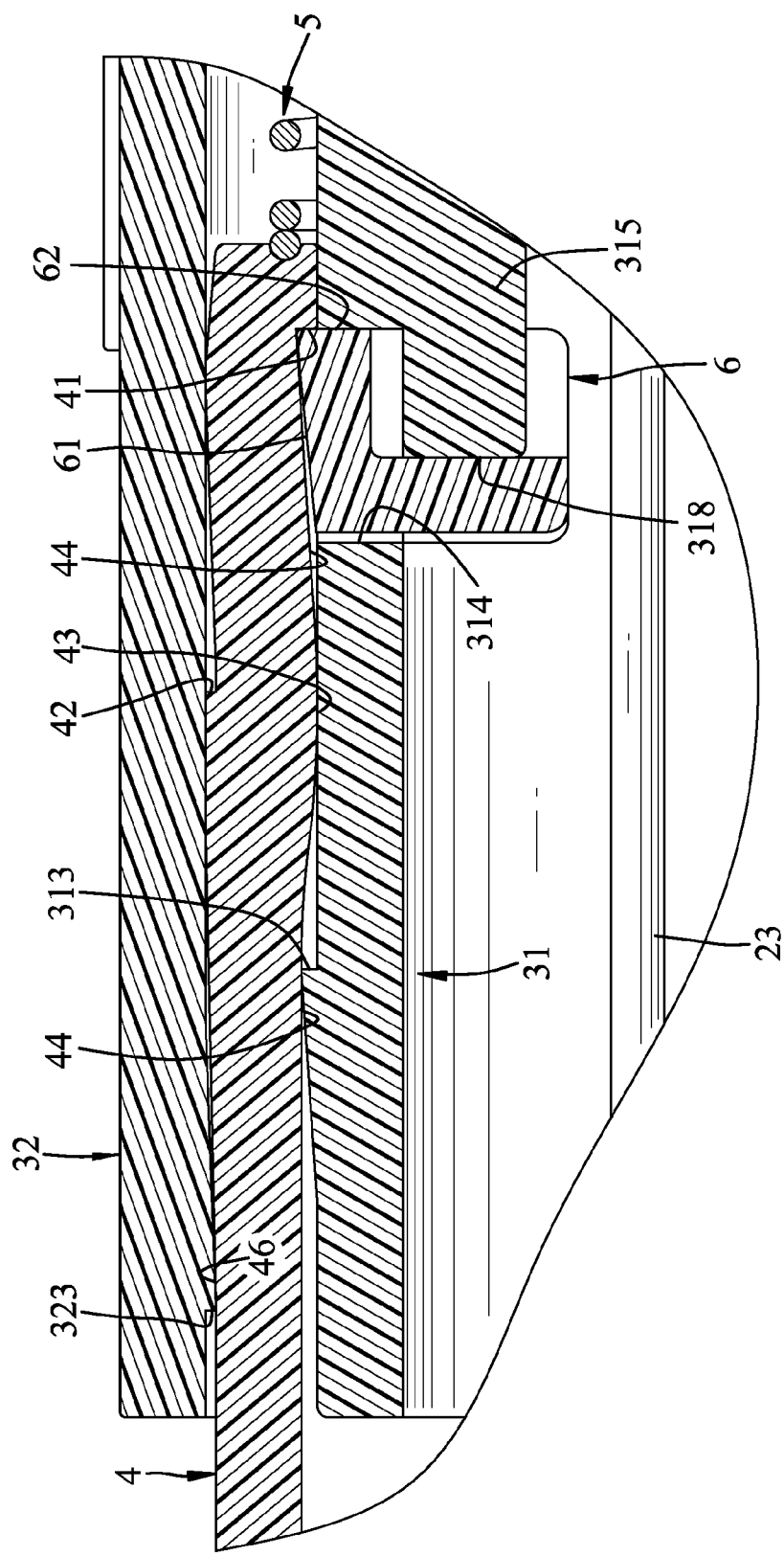
FIG. 5 is a partially enlarged side view of the needle protecting module of an injection device in FIG. 1.

With reference to FIGS. 4 and 5, the mounting tube 4 is hollow, is movably inserted into the annular space 30 and has a first engagement surface 41, a second engagement surface 42, a protrusion 43, two first recessed portions 44, and a second recessed portion 46. The first engagement surface 41 is formed on the interior of the mounting tube 4 and is adjacent to the rear end of the mounting tube 4. The second engagement surface 42 is formed on the exterior of the mounting tube 4. The protrusion 43 protrudes from the interior of the mounting tube 4 and is adjacent to the first engagement surface 41. The two first recessed portions 44 are formed on the interior of the mounting tube 4 and are respectively connected with the rear end and the front end of the protrusion 43. The thickness of the mounting tube 4 at the portion corresponding to the protrusion 43 is thicker than the thickness of the mounting tube 4 at the portion corresponding to any of the first recessed portions 44. Prior to use, the two first recessed portions 44 respectively accommodate the stopping unit 6 and the first tube stepped surface 313. The second recessed portion 46 is formed on the exterior of the mounting tube 4 and accommodates the second tube stepped surface 323.

The elastic unit 5 is mounted in the annular space 30, abuts both the mounting tube 4 and the needle base 22 bilaterally, and is mounted around the base rib 223.

The stopping unit 6 is mounted in the tube hole 314, is perpendicular to the axis X, and has an inclined surface 61 and a restricting surface 62. The inclined surface 61 is inclined relative to the axis X, is formed on the end of the stopping unit 6 distal from the axis X. The restricting surface 62 is connected with the rear side of the inclined surface 61, is accommodated in one of the first recessed portions 44 and selectively abuts the first engagement surface 41.

Figure 6:
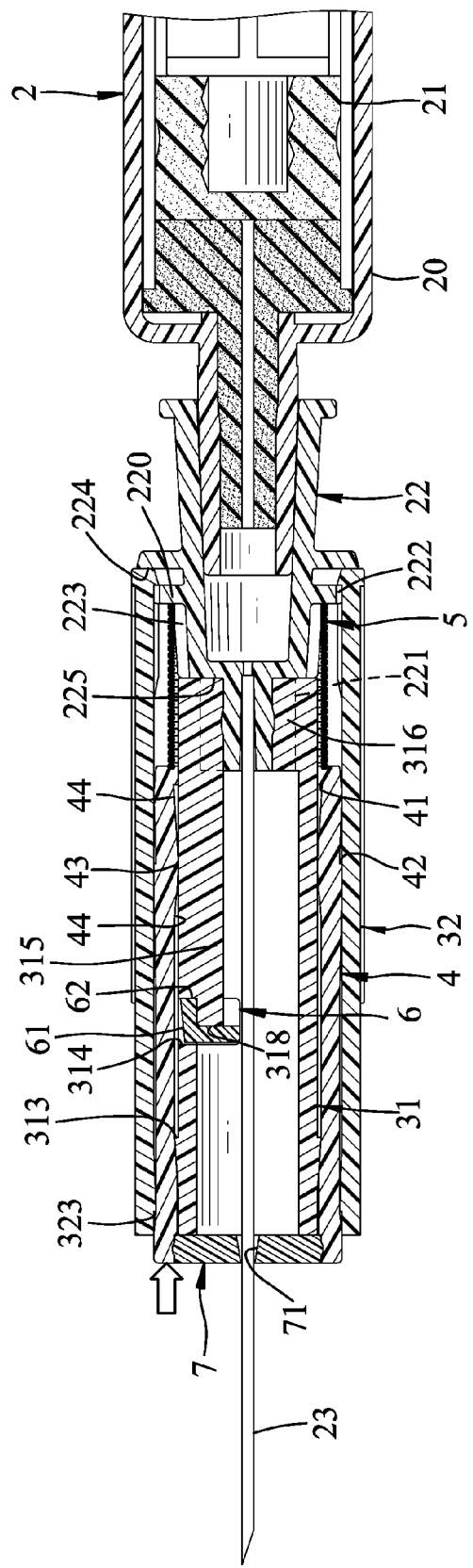
FIG. 6 is an operational side view of the needle protecting module of an injection device in FIG. 1 in an engagement with a syringe.
Figure 7:
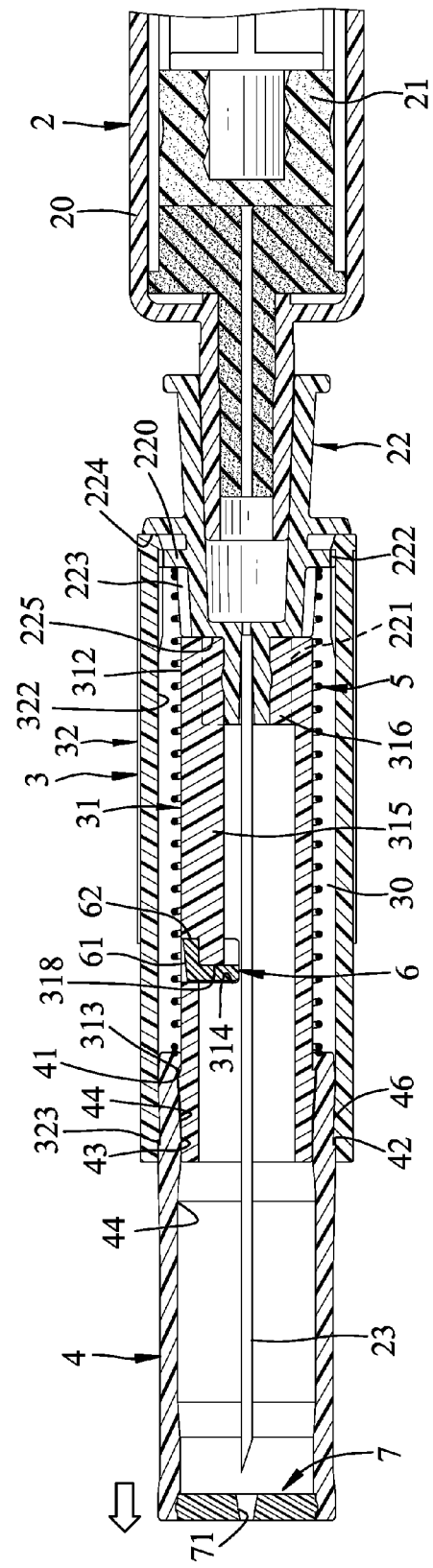
FIG. 7 is an operational side view of the needle protecting module of an injection device in FIG. 1 in an engagement with a syringe.
Figure 8:
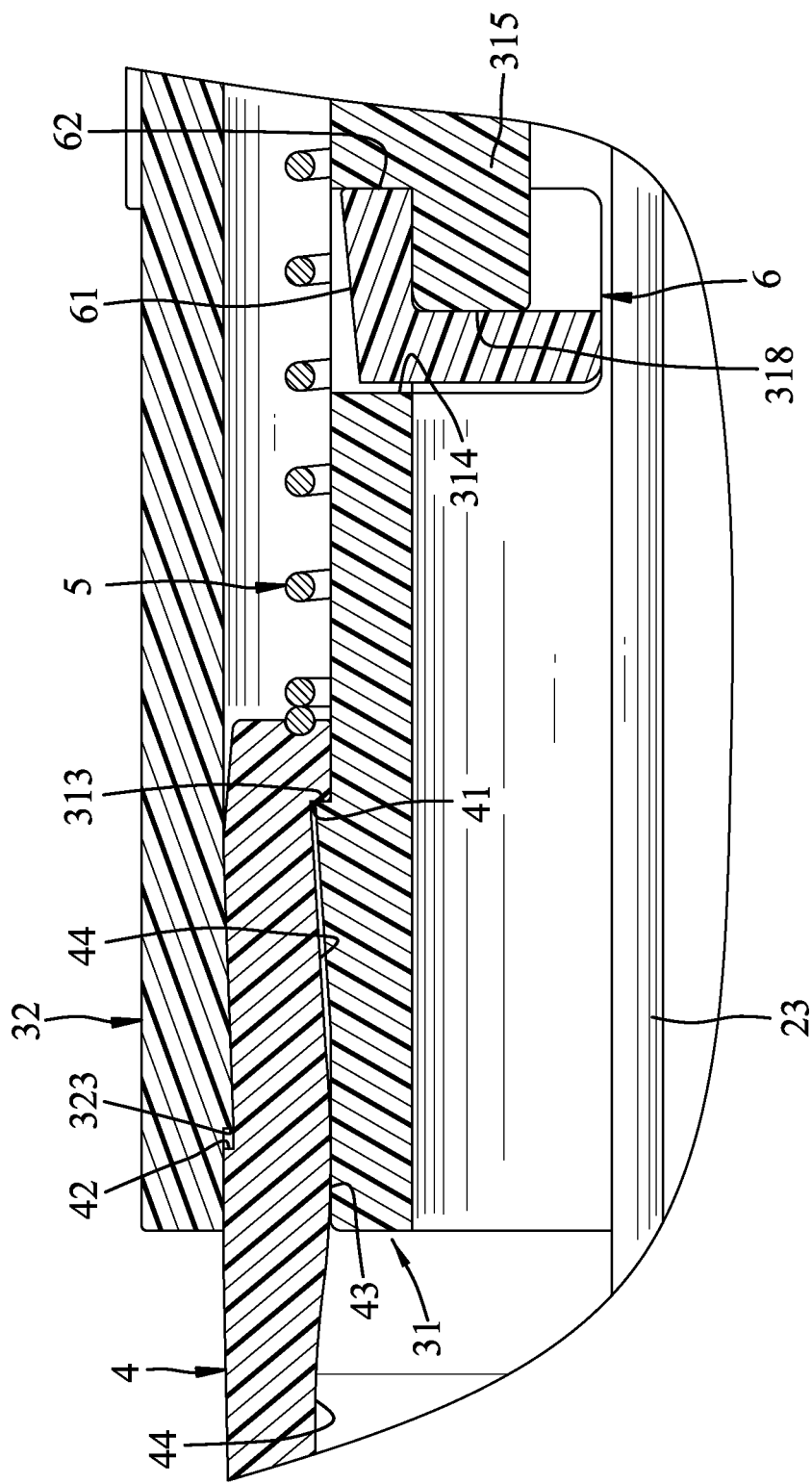
FIG. 8 is a partially enlarged side view of the needle protecting module of an injection device in FIG. 7.

In assembling, the stopping unit 6 is inserted into the tube hole 314, mounts on the tube rib 315, and abuts the abutted surface 318. The inclined surface 61 protrudes into the annular space 30 and the restricting surface 62 engages with the first engagement surface 41. With reference to the FIGS. 4 and 5, prior to use, the stopping unit 6 is firmly located at the initial position relative to the mounting tube 4 and the inner tube 31 since the mounting tube 4 is forced by the elastic force of the elastic unit 5 and the first engagement surface 41 abuts the restricting surface 62 to fix the position of the stopping unit 6. With reference to FIGS. 6, 7 and 8, when at use, the mounting tube 4 initially moves into the annular space 30 toward the needle base 22, the stopping unit 6 is pushed by the protrusion 43 to move into the tube hole 314 until the stopping unit 6 is stopped by the tube rib 315, such that the first engagement surface 41 is disengaged from the restricting surface 62

The cover 7 is mounted in the front end of the mounting tube 4 opposite to the needle base 22, has a cover hole 71 formed through the cover 7 in parallel with the axis X and provided to be inserted by and to constrain tilting of the needle body 23.

With reference to FIGS. 1 and 2, the mounting cover 8 is mounted around an end of the outer tube 32 opposite to the needle base 22 and encloses the needle body 23 and the mounting tube 4.

With reference to FIGS. 2 to 5, the assembling processes are described as follows:

1. The inner tube 31 is mounted around the needle base 22 and the annular recess 317 is engaged with the annular flange 226.

2. The stopping unit 6 is inserted into the tube hole 314 and mounts on the tube rib 315.

3. The outer tube 32 is mounted around the needle base 22 such that the tube engagement rib 320 is engaged with the plate 220. As a consequence, the annular space 30 is formed between the outer tube 32 and the inner tube 31.

4. The elastic unit 5 and the mounting tube 4 are inserted into the annular space 30 sequentially. The mounting tube 4 is moved toward the needle base 22 smoothly since the inner tube 31 and the outer tube 32 provide radial flexibility due to the presence of the first slits 311 and the second slits 321. The mounting tube 4 presses the elastic unit 5 to store the elastic force.

5. The stopping unit 6 is pushed to move away from the axis X into the annular space 30 by a fixture inserted into the inner tube 31 after the first engagement surface 41 passes the stopping unit 6, such that the restricting surface 62 is engaged by the first engagement surface 41 of the mounting tube 4 under the counter force exerted by the biased elastic unit 5.

Then, the needle body 23 is inserted into the tube module and connected with the needle base 22, is parallel with the axis X. Alternatively, the needle body 23 may be pre-inserted into and connected with the needle base 22 before the tube module 3 is mounted around the needle base 22.

6. Finally, the cover 7 having a cover hole 71 is mounted in the mounting tube 4, and then the mounting cover 8 is mounted around the outer tube 32.

In the above assembling processes, the two first recessed portions 44 and the second recessed portion 46 accommodate the inclined surface 61, the first tube stepped surface 313 and the second tube stepped surface 323 respectively, such that the movement of the mounting tube 4 during injection operation is facilitated smoothly, whereas firmly mounted between the inner tube 31 and the outer tube 32.

With reference to FIGS. 2, 4 to 6, before injection, the movable mounting tube 4 is fixed by the stopping unit 6 and the elastic unit 5 to keep the mounting tube 4 from moving away from the needle base 22. The mounting cover 8 is removed to reveal the injection part of the needle body 23 protruding out of the cover hole 71.

Then, the needle body 23 that protrudes out of the cover hole 71 targeting the skin of a patient for injection. The skin of the patient counter-pushes the mounting tube 4 during needle puncture to move toward the needle base 22 and compress the elastic unit 5. Meanwhile, the stopping unit 6 is pushed into the tube hole 314 by the protrusion 43 to abut the tube rib 315.

With reference to FIGS. 7 and 8, after the injection is finished, the needle body 23 is pulled out of the skin of the patient. At the same time, the mounting tube 4 is pushed by the biased elastic unit 5 to move opposite to the needle base 22 until the first engagement surface 41 is engaged with the first tube stepped surface 313 and the second engagement surface 42 is engaged with the second tube stepped surface 323. Therefore, the mounting tube 4 cannot be detached from the inner tube 31 and can enclose the needle body 23, such that the needle body 23 can be isolated perfectly.

Figure 9:
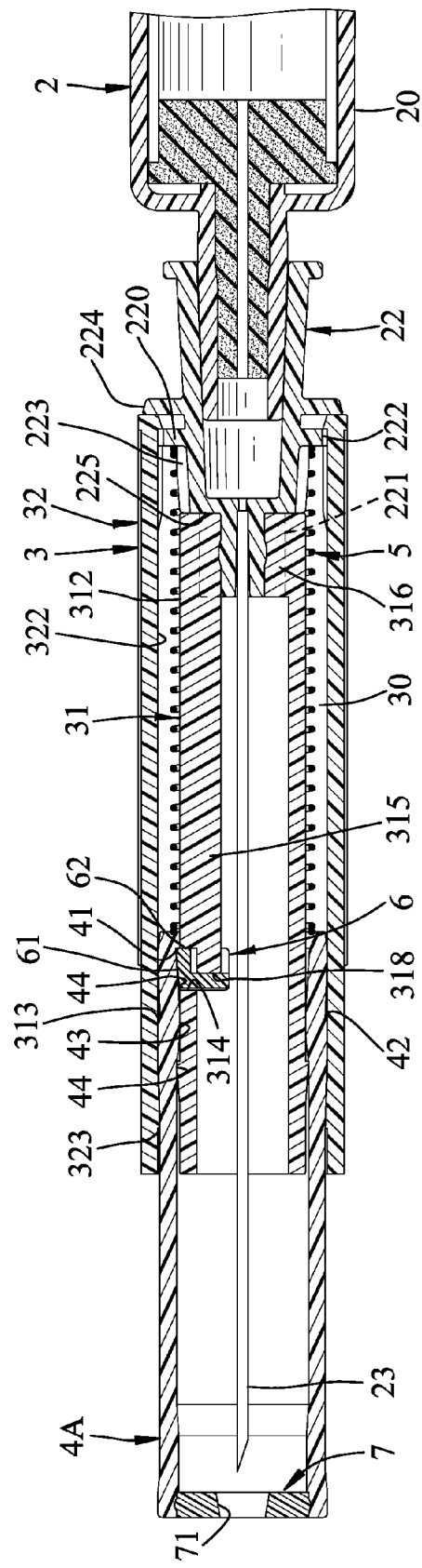
FIG. 9 is a side view in partial section of a second preferred embodiment of a needle protecting module of an injection device in accordance with the present invention in an engagement with a syringe.
Figure 10:
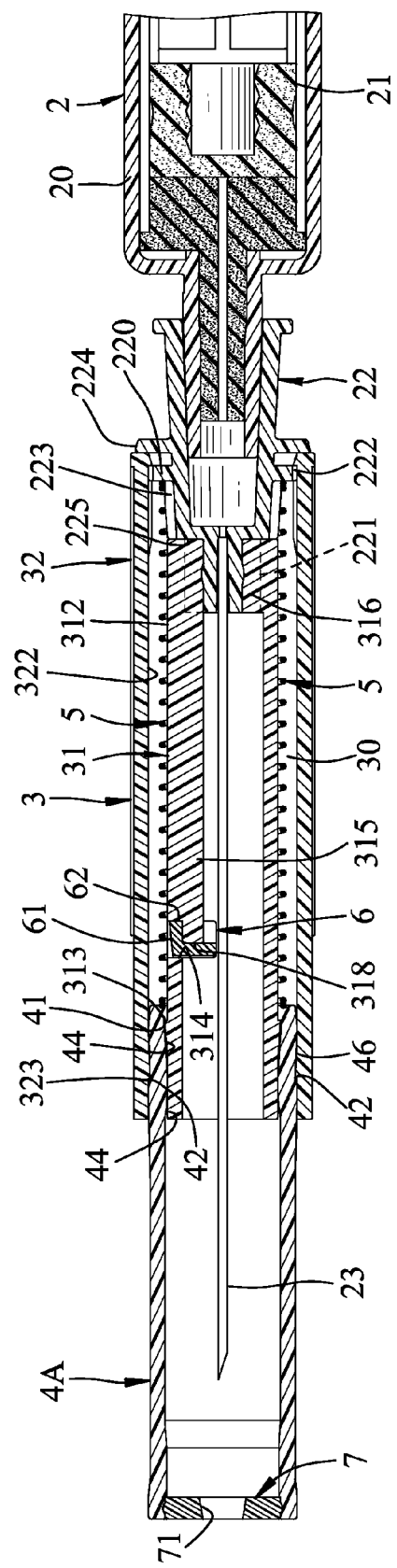
FIG. 10 is an operational side view of the needle protecting module of an injection device in FIG. 9 in an engagement with a syringe.

With reference to FIGS. 9 and 10, a second preferred embodiment of a needle protecting module of an injection device in accordance with the present invention is similar to the first preferred embodiment in features and has a mounting tube 4A. The needle protecting module is featured to enable the mounting tube 4A extended over and completely shield the needle body 23 before use. Before injection, the needle body 23 is enclosed by the mounting tube 4A to reduce the fear of the patient of needle-phobia. The operation process of the second preferred embodiment is similar with the first preferred embodiment except with the front end of the mounting tube 4A directly attached the injection target at the beginning of an injection.

Figure 11:
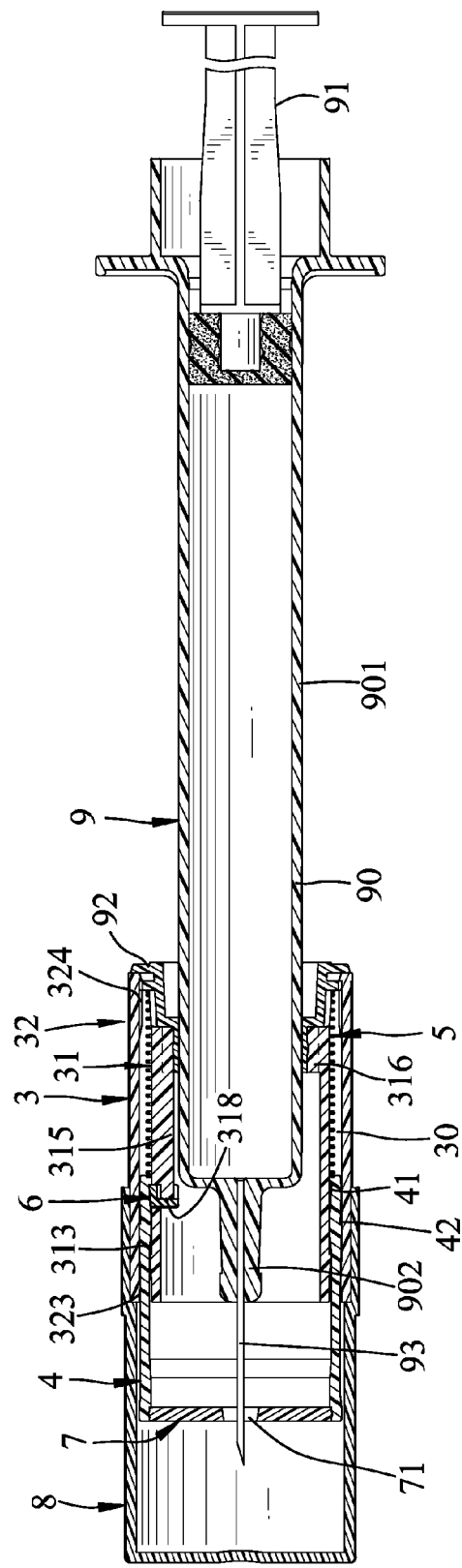
FIG. 11 is a side view in partial section of a first preferred embodiment of a syringe with a needle protecting module in accordance with the present invention.
Figure 12:
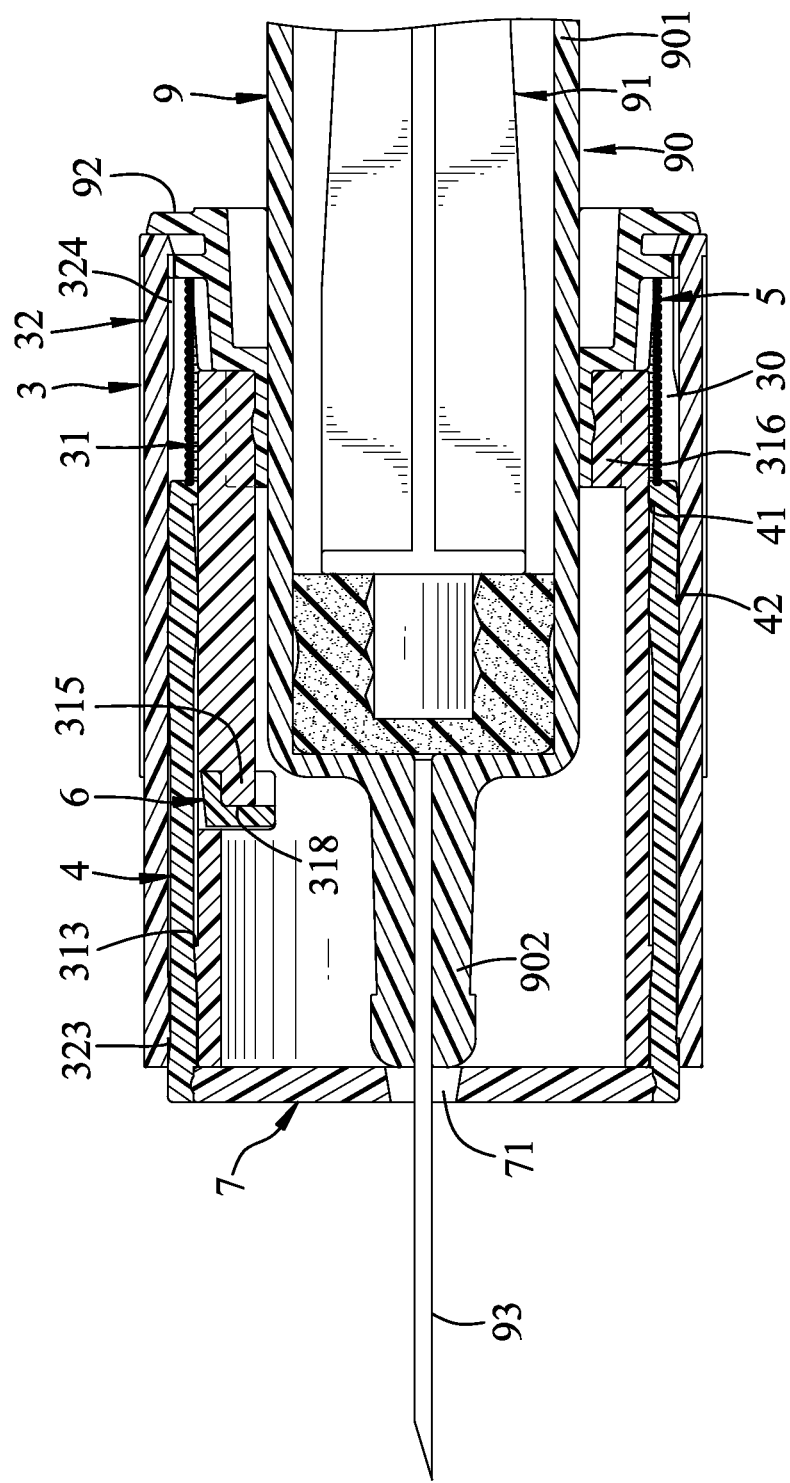
FIG. 12 is a partially enlarged side view of the syringe with a needle protecting module in FIG. 11.
Figure 13:
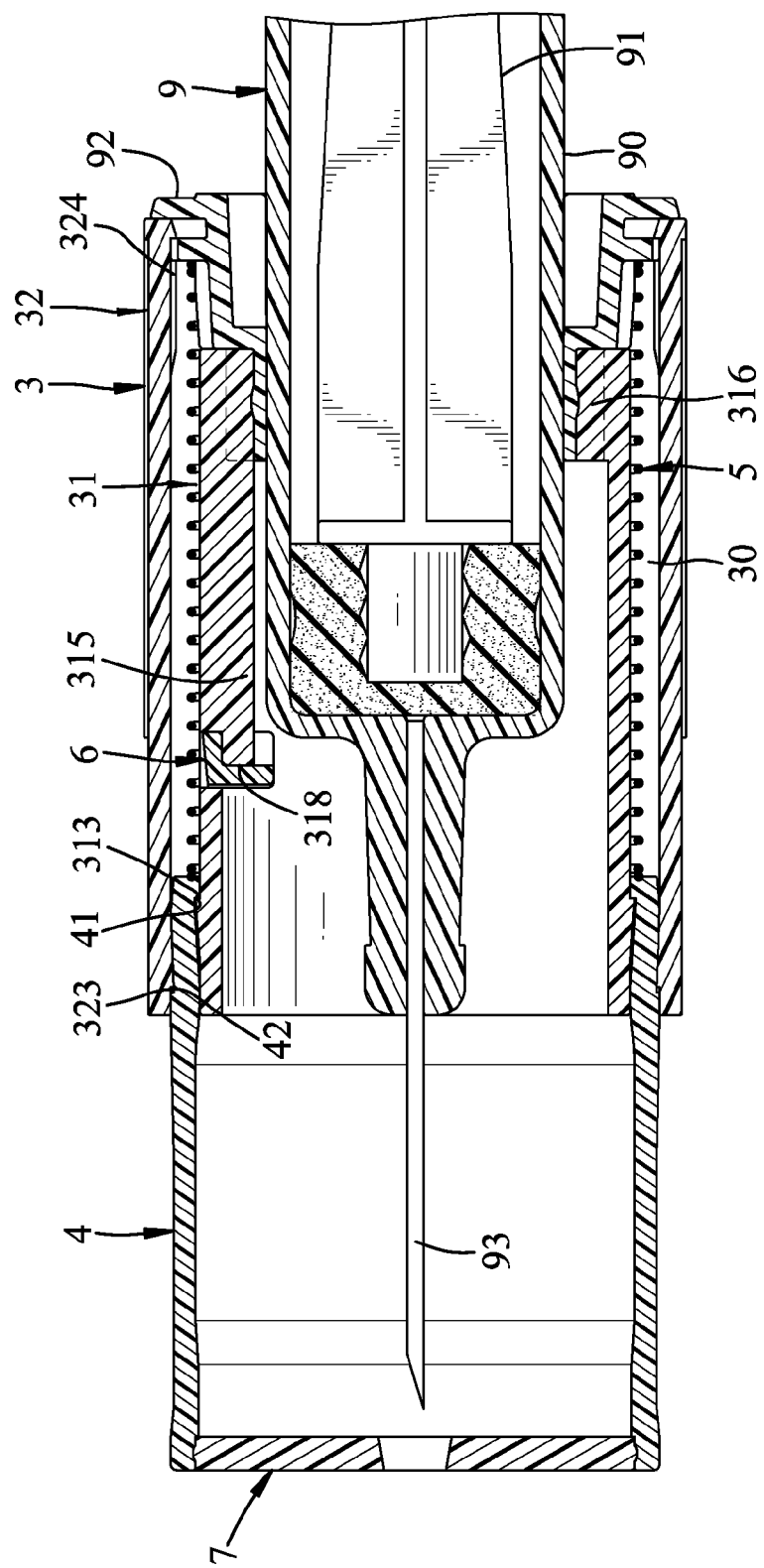
FIG. 13 is an enlarged operational side view of the syringe with a needle protecting module in FIG. 11.

With reference to FIGS. 11 to 13, a first preferred embodiment of an injection device with a needle protecting module in accordance with the present invention is similar to the first preferred embodiment of the needle protecting module of an injection device and has syringe 9, a needle body 93, a needle base 92, a tube module 3, a mounting tube 4, an elastic unit 5, a stopping unit 6, a cover 7, and a mounting cover 8. The syringe 9 has a tube body 90, an axis X, a needle body 93, and a pushing stick module 91, The needle body 93 is connected with the tube body 90 along the axis X and penetrates through the needle protecting module. The tube body 90 has a large-diameter section 901 and a small-diameter section 902. The needle base 92 is removably engaged with the large-diameter section 901. The pushing stick module 91 is slidably mounted in the large-diameter section 901 to push the medication contained in the large-diameter section 901. The small-diameter section 902 is inserted by and connected with the needle body 93. The operation process of the first preferred embodiment of a syringe with a needle protecting module is similar to the first preferred embodiment of the needle protecting module of an injection device in connecting with a syringe for medication administration.

Figure 14:
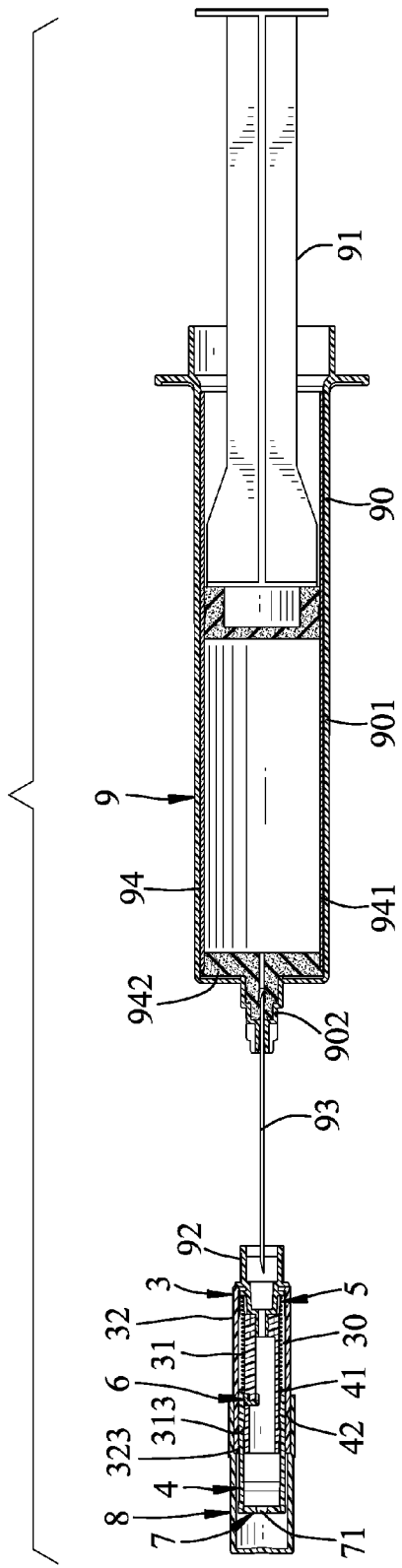
FIG. 14 is a side view in partial section of a second preferred embodiment of a syringe with a needle protecting module in accordance with the present invention.
Figure 15:
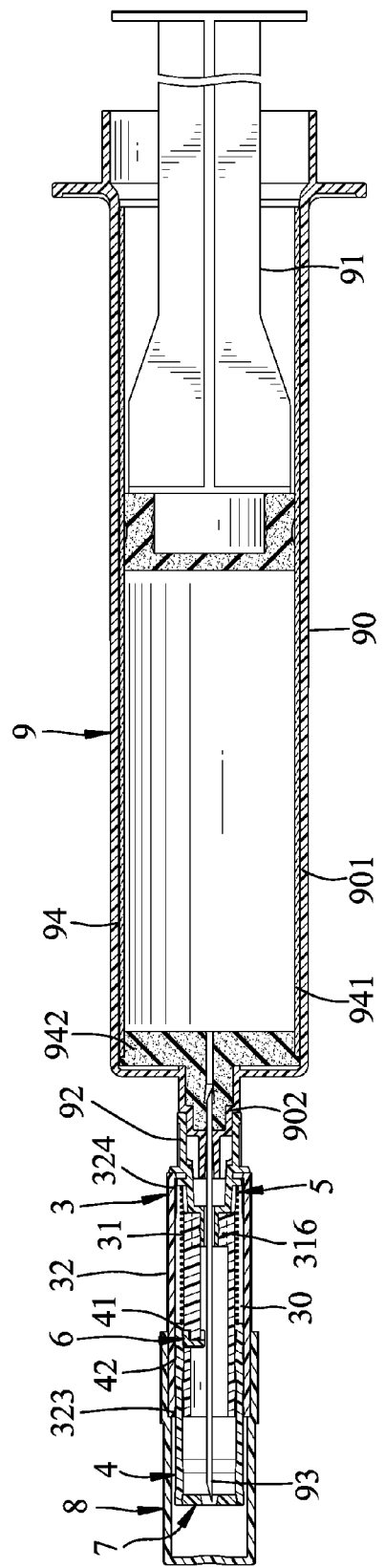
FIG. 15 is a side view in partial section of the syringe with a needle protecting module in FIG. 14.

With reference to FIGS. 14 and 15, a second preferred embodiment of an injection device with a needle protecting module in accordance with the present invention is similar to the first preferred embodiment of an injection device with a needle protecting module. The syringe 9 further has a medication tube 94 mounted in the tube body 90, a medication tube wall 941, and a plug body 942. The pushing stick module 91 is airtightly mounted in the medication tube 94. The plug body 942 is airtightly mounted on the front end of the medication tube 94 and abuts simultaneously the tube body 90 approaching the small-diameter section 902. The needle base 92 is removably mounted around the small-diameter section 902 of the tube body 90.

Figure 16:
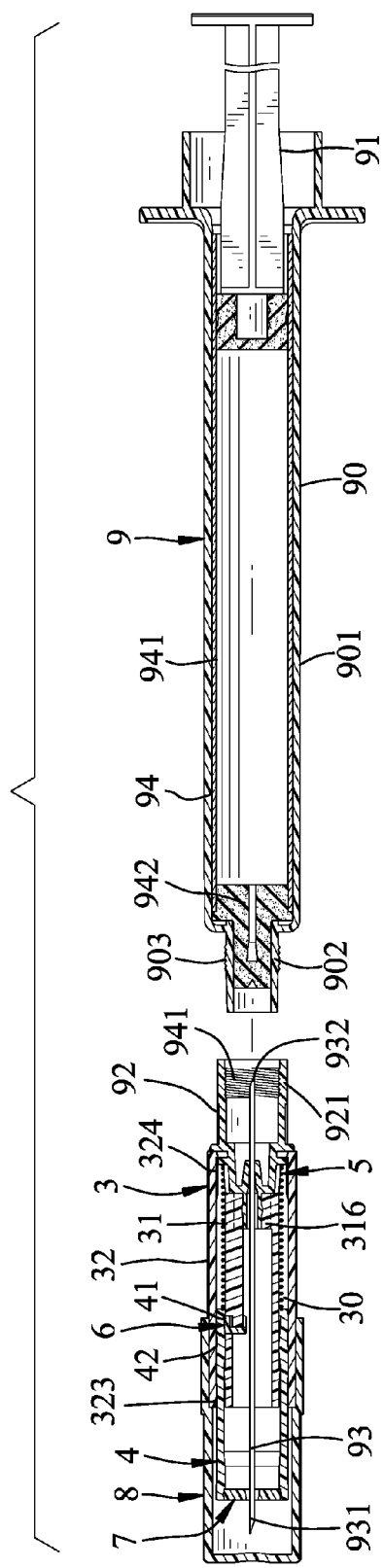
FIG. 16 is a side view in partial section of a third preferred embodiment of a needle protecting module of an injection device in accordance with the present invention in connecting with a syringe.
Figure 17:
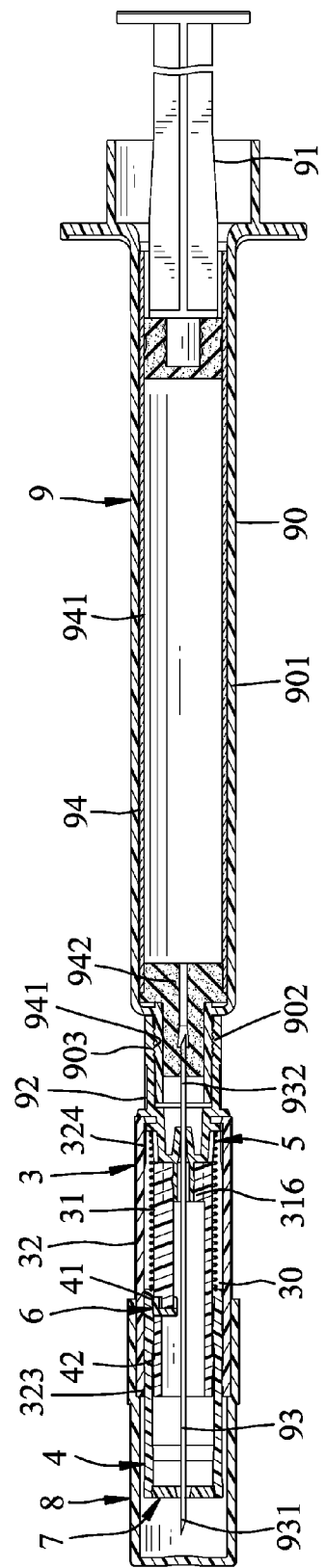
FIG. 17 is a side view in partial section of the needle protecting module of an injection device in FIG. 16 in an engagement with a syringe.
Figure 18:
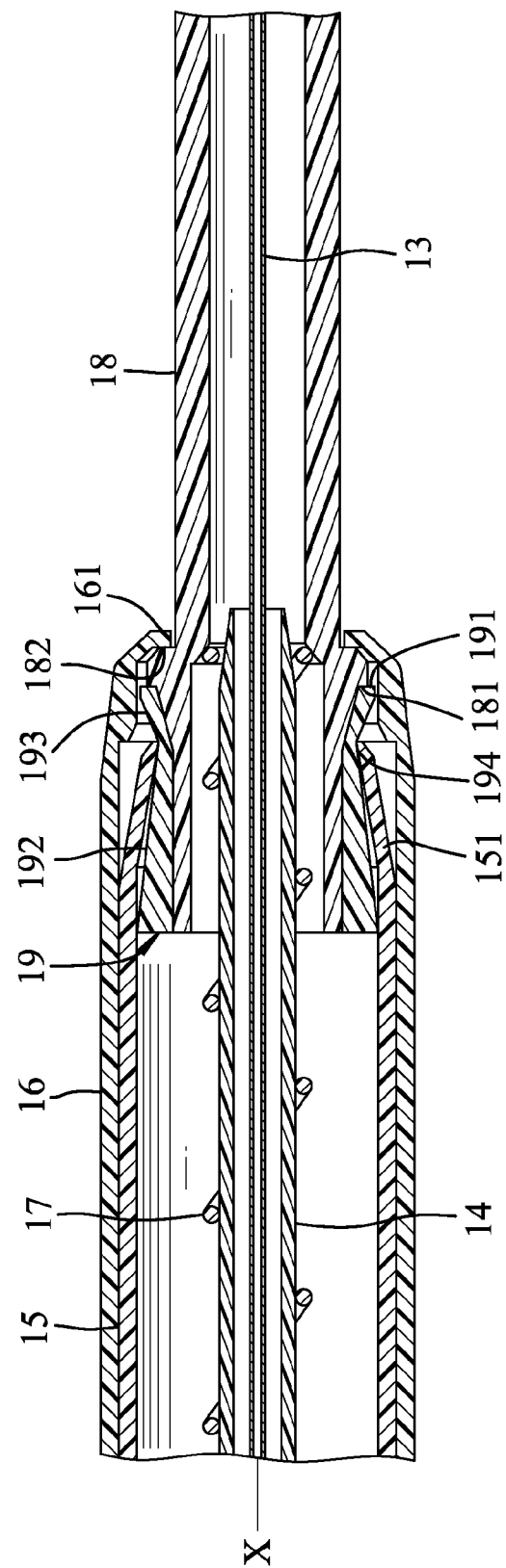
FIG. 18 is a partially cross sectional side view of a prior art of a needle set of a syringe.
Figure 19:
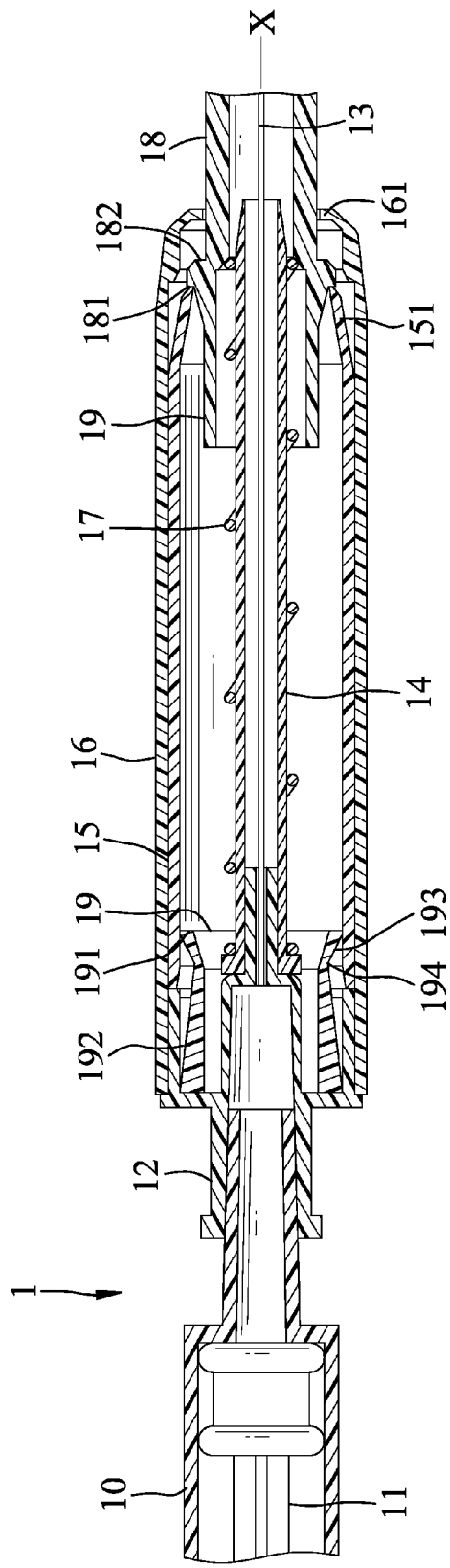
FIG. 19 is an operational side view in partial section of the prior art of a needle set in FIG. 18 in an engagement with a syringe.

With reference to FIGS. 16 and 17, a third preferred embodiment of a needle protecting module of an injection device in accordance with the present invention is similar to the second preferred embodiment of an injection device with a needle protecting module. The tube body 90 of the syringe 9 further has an outer thread section 903 formed on the exterior of the small-diameter section 902. The needle base 92 further has an inner thread section 921 formed on the interior of the needle base 92. The needle base 92 and the small-diameter section 902 are combined with each other by the outer thread section 903 and the inner thread section 921. The needle body 93 is transfixed through and connected with the needle base 92, and has a front injection section 931 and a rear insertion section 932. In the process of combining the needle protecting module with the syringe 90 the needle base 92 engages with the small-diameter section 902 by threads, the rear insertion section 932 penetrates through the plug body 942 gradually to communicate the medication tube 94.

According to the above described preferred embodiment, the needle protecting module of an injection device and the injection device with a needle protecting module provide the following advantages:

1. The packaging volume of the needle protecting module of an injection device can be greatly reduced as compared with a convention safety needle set since the stopping unit 6 is mounted in the interior tube 31.

2. The mounting tube 4 can meet the hygiene and safety demand since the mounting tube 4 can passively enclose the needle body 23 after injection to prevent infection and unintentional needlestick injury (shown in all the preferred embodiments). The needle body 23 can also be sheltered fully in the mounting tube 4 before injection to reduce the fear of the patient of needle-phobia (shown in the second preferred embodiment of a needle protecting module of a syringe). The needle base 92 can be mounted around the large-diameter section 901 of the tube body 90 (as shown in the first preferred embodiment of an injection device with a needle protecting module). The syringe 9 can further have the medication tube 94 (as shown in the second preferred embodiment of an injection device with a needle protecting module and the third preferred embodiments of a needle protecting module of an injection device). The needle base 92 can be combined with the tube body 90 by threads (as shown in the third preferred embodiment of a needle protecting module of an injection device). Accordingly, the needle protecting module of an injection device and the injection device with a needle protecting module in accordance with the present invention can have multiple embodiments to meet different demands of the users.

What is claimed is:

1. A needle protecting module of an injection device having:
   a needle base having
      an annular flange protruding from the needle base radially;
      a plate protruding from the needle base radially; and
      a stopping surface formed on a side of the plate;
   a needle body transfixing the needle base and connected with the needle base;
   a tube module mounted around the needle base and having
      a first annular surface formed as a periphery;
      a second annular surface formed as a periphery and surrounding the first annular surface;
      an outer tube mounted around the needle base, engaging with the plate, abutting the stopping surface, and comprising a front end, wherein the second annular surface is formed on an interior of the outer tube;
      an inner tube mounted around the needle base, wherein the first annular surface is formed on an exterior of the inner tube, and the outer tube surrounds the inner tube, and the inner tube further has
         an annular recess formed on the interior of the inner tube radially and engaged with the annular flange; and
         a tube engagement rib formed on the second annular surface, abutting the stopping surface, and engaged with the flange;
      an annular space formed between the first annular surface and the second annular surface;
      a first tube stepped surface formed radially on the first annular surface; and
      a second tube stepped surface formed radially on the second annular surface and being adjacent to the front end of the outer tube;
   a mounting tube being hollow, movably inserted into the annular space and having
      a first engagement surface formed on an interior of the mounting tube; and
      a second engagement surface formed on an exterior of the mounting tube and selectively engaged with the second tube stepped surface;
   an elastic unit mounted in the annular space and abutting both the mounting tube and the needle base bilaterally; and
   a stopping unit moveably mounted in the tube module and selectively engaged with the mounting tube.

2. The needle protecting module of an injection device as claimed in claim 1, wherein the mounting tube further has two first recessed portions formed on the interior of the mounting tube, wherein one of the first recessed portions accommodates the first tube stepped surface, and the other first recessed portion accommodates the stopping unit.

3. The needle protecting module of an injection device as claimed in claim 2, wherein the mounting tube further has a second recessed portion formed on the exterior of the mounting tube and accommodating the second tube stepped surface.

4. The needle protecting module of an injection device as claimed in claim 2, wherein
   the mounting tube further has a protrusion protruding from the interior of the mounting tube and between the two first recessed portions; and
   the stopping unit further has
      an inclined surface formed on an end of the stopping unit; and
      a restricting surface connected with the inclined surface and selectively engaged with the first engagement surface.

5. The needle protecting module of an injection device as claimed in claim 1, wherein the inner tube further has
   a tube hole formed through the inner tube and accommodating the stopping unit;
   a tube rib formed on an interior of the inner tube, extending to the tube hole and selectively abutting the stopping unit; and
   an abutted surface formed on an end of the tube rib opposite to the needle base and abutting the stopping unit.

6. The needle protecting module of an injection device as claimed in claim 1 further having
   a cover mounted in a front end of the mounting tube opposite to the needle base; and
   a cover hole formed through the cover and provided to be inserted by and to constrain tilting of the needle body.

7. The needle protecting module of an injection device as claimed in claim 1 further having a mounting cover mounted around the outer tube and enclosing the mounting tube and the needle body.

8. The needle protecting module of an injection device as claimed in claim 1, wherein at least one of the inner tube and the outer tube further has at least one slit formed through from an end of the inner tube or an end of the outer tube that is opposite to the needle base.

9. The needle protecting module of an injection device as claimed in claim 1, wherein
   the needle base further has multiple base engagement portions formed on an exterior of the needle base; and
   one of the inner tube and the outer tube further has multiple tube engagement portions mounted on an interior of the inner tube or the second annular surface of the outer tube, wherein the tube engagement portions match and are engaged with the base engagement portions to form a non-rotatable status of the tube module relative to the needle base.

10. An injection device with a needle protecting module for safe injection having:
    a syringe having a tube body and an axis;
    a needle body transfixed through and communicating with the tube body for medication injection, and being parallel with the axis of the syringe;
    a needle base removably engaged with and mounted around the tube body, being parallel with the axis and transfixed by the needle body, and the needle body penetrating through the needle base, wherein the needle base further has
       an annular flange protruding from the needle base radially;
       a plate protruding from the needle base radially; and
       a stopping surface formed on a side of the plate;
    a tube module mounted around the needle base and having
       a first annular surface formed as a periphery and being parallel with the axis;
       a second annular surface formed as a periphery, being parallel with the axis and surrounding the first annular surface;
       an outer tube mounted around the needle base, engaging with the plate, abutting the stopping surface and comprising a front end, wherein the second annular surface is formed on an interior of the outer tube;
       an inner tube mounted around the needle base, wherein the first annular surface is formed on an exterior of the inner tube, and the outer tube surrounds the inner tube, and the inner tube further has
an annular recess formed on the interior of the inner tube radially and engaged with the annular flange; and
a tube engagement rib formed on the second annular surface, abutting the stopping surface, and engaged with the flange;
an annular space formed between the first annular surface and the second annular surface;
a first tube stepped surface formed radially on the first annular surface; and
a second tube stepped surface formed radially on the second annular surface and being adjacent to the front end of the outer tube;
a mounting tube being hollow, movably inserted into the annular space and having
a first engagement surface formed on an interior of the mounting tube; and
a second engagement surface formed on an exterior of the mounting tube and selectively engaged with the second tube stepped surface;
an elastic unit mounted in the annular space and abutting both the mounting tube and the needle base bilaterally; and
a stopping unit moveably mounted in the tube module perpendicular to the axis and selectively engaged with the mounting tube.

11. The injection device with a needle protecting module as claimed in claim 10, wherein the mounting tube further has two first recessed portions formed on the interior of the mounting tube, wherein one of the first recessed portions accommodates the first tube stepped surface, and the other first recessed portion accommodates the stopping unit.

12. The injection device with a needle protecting module as claimed in claim 11, wherein the mounting tube further has a second recessed portion formed on the exterior of the mounting tube and accommodating the second tube stepped surface.

13. The injection device with a needle protecting module as claimed in claim 11, wherein
the mounting tube further has a protrusion protruding from the interior of the mounting tube and between the two first recessed portions; and
the stopping unit further has
an inclined surface being inclined relative to the axis, and formed on an end of the stopping unit distal from the axis; and
a restricting surface connected with the inclined surface and selectively engaged with the first engagement surface.

14. The injection device with a protecting module as claimed in claim 10, wherein the inner tube further has
a tube hole formed through the inner tube, perpendicular to the axis and accommodating the stopping unit;
a tube rib formed on an interior of the inner tube, extending to the tube hole and selectively abutting the stopping unit; and
an abutted surface formed on an end of the tube rib opposite to the needle base and abutting the stopping unit.

15. The injection device with a needle protecting module as claimed in claim 10 further having a cover mounted in a front end of the mounting tube opposite to the needle base; and a cover hole formed through the cover and provided to be inserted by and to constrain tilting of the needle body.

16. The injection device with a needle protecting module as claimed in claim 10 further having a cover mounted around the outer tube and enclosing the mounting tube and the needle body.

17. The injection device with a needle protecting module as claimed in claim 10, wherein at least one of the inner tube and the outer tube further has at least one slit formed through from an end of the inner tube or an end of the outer tube that is opposite to the needle base and parallel with the axis.

18. The injection device with a needle protecting module as claimed in claim 10, wherein
the needle base further has multiple base engagement portions formed on an exterior of the needle base;
one of the inner tube and the outer tube further has multiple tube engagement portions mounted on an interior of the inner tube or the second annular surface of the outer tube, wherein the tube engagement portions match and are engaged with the base engagement portions to form a non-rotatable status of the tube module relative to the needle base.

* * * * *